United States Patent [19]
Zöld

[11] Patent Number: 4,936,465
[45] Date of Patent: Jun. 26, 1990

[54] METHOD AND APPARATUS FOR FAST, RELIABLE, AND ENVIRONMENTALLY SAFE DISPENSING OF FLUIDS, GASES AND INDIVIDUAL PARTICLES OF A SUSPENSION THROUGH PRESSURE CONTROL AT WELL DEFINED PARTS OF A CLOSED FLOW-THROUGH SYSTEM

[76] Inventor: Tibor Zöld, Philippistrasse 13, 4400 Münster, Fed. Rep. of Germany

[21] Appl. No.: 408,392

[22] Filed: Sep. 15, 1989

Related U.S. Application Data

[63] Continuation of Ser. No. 129,729, Dec. 7, 1987, abandoned.

[51] Int. Cl.$^5$ ............................................. B07C 5/04
[52] U.S. Cl. ................................. 209/3.1; 209/552; 209/606; 209/643; 209/906; 222/420; 324/71.4
[58] Field of Search ................ 209/3.1, 3.2, 3.3, 606, 209/552, 643, 644, 932, 942, 906; 356/39, 335; 324/71.4; 222/420–422

[56] References Cited

U.S. PATENT DOCUMENTS

| | | | |
|---|---|---|---|
| 3,791,517 | 2/1974 | Friedman | 209/606 X |
| 4,175,662 | 11/1979 | Zöld | 209/552 |
| 4,237,416 | 12/1980 | Zöld | 324/71.4 |
| 4,526,276 | 7/1985 | Shoor et al. | 209/606 |
| 4,756,427 | 7/1988 | Göhde et al. | 209/3.1 |

Primary Examiner—Donald T. Hajec
Attorney, Agent, or Firm—Toren, McGeady & Associates

[57] ABSTRACT

A method and apparatus for controlling flows of fluids, suspensions, gases, aerosols, and for sorting individual particles, flowing in transporter ducts of a flow-through duct system, using for control of the flow and hence, for dispensing and sorting processes, a pressure increase for a short time interval, at the entrances of preselected ducts having a value so that the flow of the fluid or gas to be dispensed comes to a stop at these entrances and is thus constrained together with the particle to flow into ducts where the pressure increase does not take place during the same dispensing/sorting phase. The momentary pressure increase is caused at the ducts either by injection of another fluid or gas through the injection duct, corresponding to these ducts, or by generation of a gas bubble or vapor between electrodes situated at the entrance of these ducts. Buffer cavities, situated between the fast fluctuating part of the system and already processed fluid, itself flowing slowly in the drainage tubes, assure very fast, reliable and stable operation for dispenser/sorter system since through the buffering effect, each dispensing flow configuration is independent from previous configurations. The density of the processed suspension is increased during processing inside the system by special filtering/collector cavities of the same kind. The possible uses of the invention include cell sorting in the fields of cytology and cancer research, accurate, environmentally friendly dispensing of any fluid or gas, i.e., in pharmaceutical chemistry, combustion research and the distribution of very dangerous fluids and gases.

71 Claims, 3 Drawing Sheets

METHOD AND APPARATUS FOR FAST, RELIABLE, AND ENVIRONMENTALLY SAFE DISPENSING OF FLUIDS, GASES AND INDIVIDUAL PARTICLES OF A SUSPENSION THROUGH PRESSURE CONTROL AT WELL DEFINED PARTS OF A CLOSED FLOW-THROUGH SYSTEM

This is a continuation of Ser. No. 07/129,729, filed Dec. 7, 1987, abandoned.

BACKGROUND OF THE INVENTION

1. Field of the Invention

The subject invention pertains to the dispensing of fluids gases or aerosols in accordance with a preselected program, or the sorting or individual particles, such as cells, of a suspension in accordance with some of their individual physio-chemical properties, such as particle size, DNA and/or protein-content of a cell. Such a method and apparatus, therefore, is useful in cytology, for cell sorting and analysis, i.e., for example, in cancer research or for the dispensing of any fluids and/or gases.

2. Description of Related Art

Two methods of practical use, and several devices based upon these methods, are known to exist for the sorting of individual particles, such as cells and chromosomes in suspension, and, using one of these methods, a droplet dispenser apparatus has also been devised recently, as is described hereinafter. The older method is often called "the jet" or "the open method"; see, for example, "Electronic Separation of Biological Cells By Volume", by M. J. Fulwyler, Science, vol. 150, pp. 910-911, Nov. 1965, and its operation is as follows:

An approximately 10 micron thick center stream, surrounded by a shealth stream of about 50-100 micron outer diameter, is ejected through an outlet of a cavity, called the nozzle chamber, to the open air in a downward direction, as the result of a pressure on the containers of the liquids of the two streams. The particles or cells are carried inside of the thin center stream to the crossing point of a very powerful laser and the optical axis of two objectives, whereby, the particle size and one of its physio-chemical components are measured through the measurement of the scattered light and the flurorescent light emitted by the particles, respectively, which, in turn, are gathered by the two objectives. The two kinds of light impulses of the passing particles or cells are converted by photomultipliers into electrical impulses, which are proportional to the two properties of the particles. From these impulses, through electronic equipment, two histograms are obtained which characterize the type of praticle of the suspension. Simutaneously, other electronic equipment analyze these impulses and determine if a particular particle is to be sorted out of the suspension in order to be collected after sorting in the corresponding container.

An ultrasonic sound wave, having a frequency of about $5 \times 10^4$ Hz., is generated along the open stream combination by a piezoelectric transducer, so that after a few millimeters, the open stream breaks up into a stream of small droplets, source of which containing the particles to be sorted out of the suspension. During the sorting process, the stream is charged electrically at that moment when the droplets are about to break off, carrying thereby some electrical charge with them. An electrical field of a few 1000 volts/cm deflects these particles to one side or the other, depending on their electrical charge, whereafter the droplets containing the particles to be sorted are collected in their appropriate containers. Droplets containing such particles which are not to be sorted out, are not charged, and, therefore, fall vertically downward and are collected in a middle container.

Excellent cell and chromsome sortings are reported in recent works in the particle flow-through range of 700-2200 (cells or chromosomes)/sec., where, additionally, excellent distributions of the sorted pupulations are also shown; see "Analysis of Glycosaminoglycans of Flow Sorted Cells, etc." by O. C. Blair et al, Cytology, vol. 3, pp. 166-171 (b 1982), and "Separtion and Analysis of Human Chromosomes etc. ", by J. G. Collard et al, Cytometry, vol. 5, pp. 9-19 (1984). However, the rather frail shape of the open stream suggests a strong inclination towards instability, and, consequently, towards unreliability. There are, in recent works, ample comments about this type of shortcoming of the sorter; see "Multistation Multiparameter Flow Cytometry: Some influences of Instrumental Factors on System Performance", by H. M. Shapiro et al, Cytometry, vol. 4, pp. 11-19 (1983), and "Helpful Hints in Flow Cytometry and Sorting", by Ph. N. Dean, Cytometry, vol. 6, pp. 62-64 (1985).

Furthermore, in this open flow system, the stream combination can also be easily disturbed by the very same particles (cells) which are to be processed if these particles are too large relative to the stream diameter; see "The Influence of Particles on Jet Breakoff", by R. T. Stovel, J. Histochem. Cytochem., vol. 25, No. 7, pp. 813-820 (1977). Finally, the use of a very powerful light source, such as a laser, is also of some disadvantage in some cases because of its bulky nature. Such a powerful light source is needed here because only objectives of low light gathering capaabilities can be safely combined with the open jet stream in order to avoid wetting of the objective by the stream itself; and the use of high power lasers can be of some further disadvantage at some places where safety regulations also have to be taken into account.

Recently, an apparatus for the dispensing of a fluid was devised, using "the jet" method for this purpose. In this system, the fluid to be dispensed flows in a stream of uncharged droplets and the amount of its flow to the target place is controlled by another charged stream of droplets through the collision of the droplets of the two streams; see "Ballistically Controlled Nonpolar Droplet Dispensing Method and Apparatus", U.S. Pat. No. 4,341,310 to Sanjiovanni et al, issued Jul. 27, 1982. This dispenser system of "the jet" type, however, cannot be easily used for the dispensing of environmentally unfriendly fluids, and only one stream can be modulated with it.

The various shortcomings of the first method or of the systems derived from it, as described above, have been known for a long time and for this reason, the search for an improved method has been well justified.

The second method for the analysis and sorting of particles in suspension was devised by applicant around the end of 1976; see Fed. Rep. of Germany Specification P 2716095, Apr. 12, 1977, and U.S. Pat. No. 4,175,662 (1979). The second sorting method functions in the following manner: The combination of a very thin center stream and its enveloping sheath stream is generated in the nozzle chamber, in a superficially similar manner as in the first method. However, the stream combination continues to flow in the shallow main channel, itself having a cross-section comparable to that of the jet stream of the first method, and since not only the nozzle chamber and the main channel, but also the other three outlet channels, which are branching out at the end of the main channel, are covered by the same very thin, about 100 microns thick, microscope cover glass, all the various streams flow in a completely closed channel system. In this system, the cells or particles flowing inside of the center stream, are analyzed typically by an optical system, wherein the articles are illuminated by an UV-light, generated by a high pressure mercury lamp of 100 watts, giving about a 10 mwatt UV-light, through a UV-objective of very high light gathering capability, being part of a microscope of the epi-illumination type, whereby, the flurorescent light, emitted by properly dyed particles, is collected by the same objective and these light impulses are converted into electrical impulses by a photomultiplier, which is part of the same microscope system. Since the light gathering capability of this objective is around 20 to 30-fold larger than those of the first method, therefore, such a simple lamp, as described above, is able to provide the same fluorescent light as a 4 watt Argon laser, which gives out about 80 mwatts power in the quasi UV range.

After analysis, the particles continue flowing inside the center stream towards the channel branching volume, while the corresponding electrical impulses are analyzed by electronic equipment which decides if the particles are to be sorted from the suspension or not. In the "two-population" mode of sorting, where two groups of particles or cells are separted from their suspension, if the particles are to be deflected to flow in the left outlet channel, in order to be sorted out, then, through electrolysis, an amount of gas is generated in the right and middle outlet channels such taht these channels are unable to draw the electrolyte therein from the channel branching volume, and, thus, the properly arriving particles to the channel branching volume are drawn into the left outlet channel with some of the surrounding electrolyte because in this channel, gas generation did not take place and therefore its drawing capability was not reduced during the time of deflection. Naturally, if the particles are to be deflected into the right outlet channel, because they belong to the second group to be sorted out, then gas is generated in the left and middle outlet channels, while particles not belonging to either of the two group are not deflected anywhere and, therefore, they leave the flow system through the middle outlet channel. Obviously, all three partial suspensions are collected in three separate bottles, which are connected to the same suction pump, which creates about a 300 mmHg pressure, i.e., a vacuum, to draw the electrolyte through the flow system into the bottles, whereby, also larger gas bubbles are generated than at atmospherical pressure. In the "one-population" mode of opeation, the particles belonging to the group, are not deflected and, therefore, they leave the system through the middle outlet channel; all the other particles are deflected, however, intermittently into the left and right channels in order to load the sorter symmetrically, and are usually thrown away as waste. Since, in this mode of sorting, the component particles always remain in pure electrolyte, if gas is not generated in the middle outlet channel. Therefore, this mode of operation is especially useful for the sorting of live cells in accordance with some of their physiochemical properites. Indirect tests show, however, that the "two-population" mode can also be used for the sorting of live cells, although, probably only with some limits as far as the length of the sorting operation is concerned because mouse tumor cells were found to live for as long as two hours in such electrolyte which was "contaminated" by the by-products of electrolysis of the physiological saline water.

Sorting results and additional observations have shown that devices of this method are indeed very stable and reliable. Center streams having thicknesses of about 1.0 microns were not found to waver under a 50-fold stereo microscope, where these steams were contrasted from the sheath streams by staining the former with black ink. Sorting of fluorescent latex beads of about 20 microns diameter was very successful with a device constructed on the basis of the second sorting method; this is a bead diameter where the first method or devices, constructed on the basis of it, are not usable; see the Stovel reference. The sorting of smaller beads, in the "two-population" mode, defined earlier, was also found to be very reliable, showing that this sorting method is indeed capable of sorting two groups of particles simultaneously. Similarly, the sorting of "one-population" of cells was also of high reliability. However, sorting results in the "two-population" mode have shown that very soft, jelly-like cells do not slide on the walls of the channel system when they flow with a very high velocity, because, in such a situation, they might disintegrate after such an encounter with the walls as a result of rubbing against the walls of the channel which are never perfectly smooth. However, at the end of the development of the latest sorter device, the deflection of the cells in this device was large enough to obtain excellent sporting results even in this case. At the end of these experiments, a broken electrode tip, and the form it followed, reduced sorting quality, and have shown the importance of the large enough cell deflections as was described above.

However, many of the "two-population" cell sortings were only of partial success, if the number of cells of one component was considerably larger than that of the other component. An additional observation has shown, furthermore, that, by fluorescing cells contrasted, the center stream has bent away, on the average, from that side channel where the deflecting gas bubbles were generated, favoring, thereby, further deflection of the cells. As a consequence of this, the larger cell population component was better sorted than the cells of the other population for which, in some cases, only debris was obtained as sorting results, which indicated very clearly that cells of this population were not deflected far enough from the channel walls. This shortcoming of the device has been so interpreted that the generated gas was not cleared away from the corresponding outlet channel, whereby, a reduction of the vacuum in this channel permitted a relatively stronger suction in the other outlet channel with the concomitant bending of the center stream and the rather poor sorting results of such sortings where one component population was larger than the other. The relatively slow clearing away of the generated gas in this device suggests also, rather strongly, that sortings of the order of several thousand cells per second with this system is rather unlikely.

There was no fluid dispensing attempted by the second method, for reasons of lack of interest for this type of operation at that time. However, it is easy to see that some variations of this type of operation are also readily possible with these devices if the gas bubbles are produced in accordance with a preselected program, defined by electronic equipment, such as a computer.

In U.S. Pat. No. 4,526,276 of shoor et al, the main geometrical and electrical characteristics are that the particle suspension is controlled to flow either inside of a tube, loacted quasi coaxially inside of a larger tube, or between these two tubes by using, for the flow control, the generation of an undefined type of gas production. While the patent claims contructional simplicity relative to the flow system described in U.S. Pat. No. 4,175,622, since, although the construction of the two coaxial tubes seems to cause no particular problem, on the other hand, the implementation of the control electrodes into these tubes is definitely not easier than the same type of electrode embedded into the vertical and easily observable and reachable walls of the channel system of the '622 Patent. One aspect is very clear, the two cylinder flow system permits only one-population sorting, while the channel system of the '622 Patent permits, optionally, either a single or double-population sorting, or even multiple sorting. Consequently the '276 Patent does not dominate the '622 Patent. For the sake of clarity, it is also important to note that the particles are indirectly sorted in both systems through the deflection of a small volume of the electrolyte, which surrounds the particles.

SUMMARY OF THE INVENTION

It is an object of this invention to provide a method wherein a vacuum compensating device is incorporated in order to eliminate one of the above shortcomings by assymetrical, and/or very fast cell sortings.

In particular, the object of this invention is to provide a method for the fast and reliable sorting of individual particles in suspension in accordance with one or more of their physio-chemical properties, or for the fast and reliable dispensing of any kind of fluid, gas, or aerosol in accordance with a preselected program, wherein the substance flows through a closed or hole-like flow system, regardless of whether or not the same rate of the fluid or suspension exists in all of the outlets of the system. Furthermore, the devices are constructed in such a manner that the whole flow system is easily observable and, therefore, cleanable through the various inlet and/or outlet tubes without opening the flow system itself, whereby, the maintenance of this device is considerably easier than earlier ones. Additionally, all the various geometrical and physio-chemical parameters, involved in the construction and operation of the system, are optimized to a very high degree, in order to obtain devices with considerably improved operation.

Accordingly, a method is decribed for the control of the flow of fluid substances, such as fluids, gases, aerosols and individual particles (cells) of a suspension, either in accordance with a preselected dispensing program, in one mode of operation, or in accordance with one or more individual physio-chemical porperties of these particles, in another mode of operation, where the substance flows through a closed, or hole-like, and environmentally friendly, duct system under the effect of a pressure difference, created between the inlets and the outlets of the system, and where a combined compensating process assures fast and reliable achievement of each preselected flow configuration, defined by the distribution of the flow of the substance to be dispensed and the flow of the injected control substance, a fluid or gas, in the outlet ducts, and the return of the flow to its steady state flow configuration after each dispensing flow configuration during the whole operation of the system. The method includes transporting said fluid substance in one or more streams in at least one transporting duct towards a duct branching volume; analyzing the individual particles in said transporting duct in accordance with one or more of their physio-chemical properties in the sorting mode of the operation; determining the proper dispensing flow configuration by an electronic system; creating the corresponding dispensing flow configuration in said duct branching volume, where not only the transporting duct enter but also at least two dispensing ducts branch out in all possible directions, by injecting a fluid control medium, a fluid or gas, at the entrance of those dispensing ducts where the substance to be dispensed or sorted is not to enter, at such a pressure that the substance to be processed is constrained to enter into those dispensing ducts where such a pressure, i.e., injection, is not caused during the same dispensing phase, meanwhile, it is the control medium that flows in those dispensing duct where the substance to be dispensed is prevented from entering; transporting the dispensing substances in their own dispensing duct toward a corresponding buffer cavity and transporting simultaneously the control medium, also in its own dispenser duct, toward a similar cavity, situated at the end of each dispenser duct; decoupling, through the fluid-free large volume of said cavity, the rapidly fluctuating small mass of the substance and the medium, flowing from said dispenser ducts into the corresponding buffer cavities, from the already processed and relatively large amount of the fluid substance, which now flows slowly out of the buffer cavities since each of these cavities is of enormously larger fluid-free volume than that of the whole dispensing flow system, whence very fast fluctuations of the small amount of the substance to be dispensed is possible and from where very fast operation of the dispenser/sorter system also follows; buffering, simultaneously in said very large cavities, the pressure fluctuations, if needed, where the latter fluctutation is caused by the also fluctuating influx of the control medium into these cavities; separating said control medium from said dispensing substance, or from the sorted particles, if this substance is a gas, by forcing this gas to leave under the effect of buoyancy through the gas outlet hole, itself being situated at the upper part of said cavity, meanwhile, the dispensed fluid leaves the cavity through an outlet hole situated at the bottom of the cavity, making, through this type of buffering, the exact return of the pressure and flow conditions of the dispensing part of the system to its steady flow state possible, whereafter, said system is ready for another prescribed dispening phase and through these compensating proceses, a fast and reliable dispensing/sorting system is obtained; directing thereafter the dispensed fluids through a two position valve either to their corresponding filtering-collector cavity, where the particles of the suspension are separated from most of the suspending fluid, obtaining thereby optionally a very highly concentrated particle suspension as an end result of the sorting process, or directing by this value this same fluid into a waste container; this mode of flow, however, is necessary only at the starting phase of the operation when the various parameters, such as the flow, the pressure difference, the deflecting means, etc., are adjusted to the particular mode of operation. It is imporatnt to note that the two position valve and the filtering-collector cavities can also be located outside of the device if that is more appropriate for a particular mode of operation; in this case said cavity is called the filtering-collector bottle, which is connected through tubes to the main part of the dispensing/sorting embodiment.

According to the invention, the method is further charcterized by the following attributes and means, which either have to be applied in accordance with the particular application of the method, or serve to provide a very high quality of operation for it. Accordingly, the flow of the substance to be processed is caused either by the application of pressure at the entrances of the flow system, embodying the method, or through the creation of a vacuum, applied at the outlets of said system, although, if it is necessary, then both causes can also be applied simultaneously, extending thereby the applicability of the method to a very large variety of cases. Furthermore, the fluid substance of the transporting duct may occupy the whole cross-section of these ducts, or said substance may be a combination of various substances, combined together, in this case, in a chamber constructed for each particular case, and if said fluid is a combination of one or more thin streams, being surrounded by an enveloping fluid, then said streams and said enveloping fluid are combined together in a nozzle chamber. One version of this nozzle chamber is described in copending U.S. patent application Ser. No. 598,151, filed Apr. 9, 1984, which is charcterized by it very high stability and reliability of creating such types of streams. Naturally, stable and reliable operation of the sorter/dispenser part is impossible without an also stable and reliable nozzle chamber.

At the steady flow configuration, the stream combination flows either through the same dispenser duct or through different ones. However, during the dispensing process, said streams flow into the prescribed dispenser ducts in accordance with the requirements posed on the system.

According to the invention, in order to achieve fast flow and rapid fluctuations of the fluid during dispensing of it, not only it is necessary to incorporate said buffer cavities into the embodiment, but, obviously, the causes of the flow, i.e., the pressure difference imposed on the embodiment, has also to be as high as possible while the amount of the substance and the control medium have to be kept at a required mimimum value. Therefore, the cross-sections of the various ducts have to be of the permissible minimum size, being limited by the particle size and/or the size of the expected extraneous pieces which might flow into the system through the prefiltering system, attached to the entrances of it; the length of the ducts being also limited by the various functional, constructional and maintenance requirements, about which further precisions are given below.

Accordingly, the place of the injection of the control medium has to be situated partly at the entrance of the dispenser ducts and partly it should be situated even slightly inside of the duct branching volume since, in this manner, the amount of the substance that has to be shaken, back and forth, in this region during the dispensing phase, is reduced to a minimum value, whereby another optimized parameter is obtained for the fastest possible operation of the system.

According to the invention, if only pressure causes the flow of the substance to be processed by the system, then the injection of the control medium takes place through the injection hole at such an injection pressure that said control medium causes a full stop of the flow of the substance into those ducts, meanwhile it is the control medium that flows into these dispenser ducts during the dispensing phase. The injection of the control medium occurs through the injection hole, having its injection outlet at the optimum place for the injection, while its inlet is situated somewhat further away from the channel volume, whereby even a large number of bulkier valves too, such as electromechanical valves, can be arranged easily, in a fan-like manner, around the duct branching volume. For the control medium, some sort of inert gas is used if chemical reactions or mixing between the substance to be processed and the control medium is to be avoided. However, if some sort of a mixing is required, then, for the control medium, the substance to be mixed is to be used. In general, however, the use of a gas as a control medium is desirable since, in this case, the amount of mass to be fluctuated during the dispensing phase is of a minimum value, whereby again the total mass to be fluctuated is reduced and, therefore, the speed of the system is further increased.

According to the invention, if the fluids flow through the system under the influence of a vacuum created at the outlets of the whole flow system, then the use of a gas as a control medium, injected through the injection duct, is used as one possiblility; in this case, an electromechanical or piezoelecctrical valve controls the injection process. However, if the substance to be dispensed is of some kind of a liquid, then a gas or vapor, injected, or more properly created, through some electrical or electrochemical process, is especially advantageous here as a control medium because the gas or vapor can be generated, in many cases, right at the optimal place of its injection defined earlier, instead of being led to that place through an injection duct where the injection process is manipulated through bulky valves. Such types of gas and vapor generation processes are, (a) the electrolysis of a properly chosen electrolyte, such as a physiological saline water, which is especially suitable for all cell processings, (b) the vaporization of a fluid, which can be the same kind of electrolyte defined above, between two electrodes through ohmic heating, provided by a very short and well stablilized electric arc or spark, or (c) through dielectric heating, created by one or more sufficiently powerful lasers. It is easy to see that all of these gas or vapor generation processes are characterized by a very high speed of operation where no moving mechanical parts are involved since the generation of these media takes place between stably constructed parts and, therefore, they work with both high speed and very high stability, i.e., with very low jitter, relative to any electromechanical valves, described above. From these aspects, it follows that the electromechanical valves should be used only in such cases where none of the gas/vapor generation processes can be used, where such are the case of gas or aerosol processings.

In accordance with the invention, the control gas has to be created at the entrance of the corresponding dispenser duct, which is called the only control duct if this duct is used only for flow control purposes, and carries none of the particles processed by the system. Here, the volume of medium generation takes place at the optimum place, defined above, i.e., partly inside of the duct itself and partly in the duct branching volume, in order to reduce the amount of the fluid to be shaken during the dispensing phase to a minimum value, increasing thereby the speed of the operation.

The electrodes, if they are applied, are placed stably in the walls of the channel system at the most appropriate place and are of very hard, heat and corrosion resistanct materials, such as platinum, molydenum, wolfram or tantal metals.

According to the invention, for an optimized dispensing/sorting process, not only the place and duration of the injection of the control medium is important, but the length of the corresponding dispenser duct has also to be so long that the control substance, injected or generated during each dispensing phase, can develop in said duct in its full length before its low stream end enters into the corresponding buffer cavity because, it is easy to see that such an incomplete development of the injection/generation process causes an adverse effect on the closing of the corresponding dispenser duct and hence, also on the whole dispensing phase.

According to the invention, where gas or vapor is used as the control medium, the vacuum has to have a very high value at the places of injection. For this reason, the hydroynamical resistance of the transporting duct has to be as high as possible, from where it follows that these ducts have the smallest permissible cross-section and the maximum possible length. Furthermore, if these ducts are so long that for a particle to be sorted, the flow-through time would be so long that, as a consequence, the operation of the system would be too slow, since, for obvious reasons, only one particle is permitted to flow between the analyzer and the duct branching volume during the processing of each particle, then this analyzer volume has to be positioned somewhere along the transporting duct, without being too close to the duct branching volume in order to let a long enough time for the deflection of the particle carrying thin stream to be completely deflected by the time when the particle to be processed arrives at the duct branching volume. There are at least three reasons for the maximum system vacuum, (a) the higher the system vacuum, the larger the force acting at dispensing the fluid to be dispensed, from where, also the higher the speed the operation follows, (b) the higher the vacuum, the larger the gas volume, produced through the generation of the same amount of gas in moles during electrolysis or heating, this fact follows from the gas laws, and from here follows also that since the gas is generated through an eletrical impulse, then for a certain gas or vapor volume, the energy to generate it is also smaller for a higher system vacuum. From reasons (a) and (b) follows a third reason (c) if the generated gas is known or suspected of having a damaging effect on the particles to be processed, then the larger gas volume produced by the minimum amount of gas in moles causes less damaging effect on these particles if these particles get into contact with the gas bubbles of such type because such bubbles contain a smaller number of damaging molecules then if the same gas volume is generated at a lower vacuum. Such contact might take place in the buffer cavities if the gas is not removed from these cavities within a very short time, which is reduced to a fraction of a millisecond if the gas is removed from the cavity through a special gas outlet hole, located at the upper part of the cavity. From this requirement follows another one of the construction nature: although the length of the dispenser ducts must be at least so long that it permits undisturbed injection or generation of the control gas, nevertheless, in order to reduce the possibility of any contact between the particles and the gas bubbles to a negligible extent, the length of the ducts must not be too long either, in order to aviod such undesired contacts, while the cross-section of these ducts has to increase towards their entrance into the corresponding buffer cavity, in order to facilitate easy separation of the gas bubbles from the electrolyte through the effect of buoyancy and, hence, from the particles.

According to the invention, in that case, where a duct is used only as a control duct, in which duct only particle free electrolyte flows, this duct has to be long enough to satisfy the requirements described above, however in this case, the electrolyte has to flow out of the buffer cavity in such a manner that it blocks nowhere the flow of the control gas, so that the buffer cavity, for the most part, always remains fluid free and is always in "air contact" with the waste bottle during the whole operation of the system, whereby, a continuous removal of said gas is assured during the device's operation.

According to the invention, the buffer cavity has two different versions, depending on the way the control gas is removed from them. In the first version, the elcectrolyte flows out of the cavity through an outlet at its bottom side, which has such a large diameter that both the dispensed electrolyte and the control gas flow out of it in parallel to each other and always in the downward direction, i.e., without forming a syphon-like bending in the tube that connects the cavity with the waste bottle itself being connected to the system vacuum pump, which causes the flow of the electrolyte in the whole system. In the second version, the gas is separated very fast from the already processed suspension and leaves the cavity through the gas outlet hole, itself being situated at the upper part of the cavity, becaause, in this second version, the suspension outlet hole, situated also at the bottom of the cavity but having a diameter which is so small that a small amount of the already processed particle containing suspension always remains in the cavity and thereby the downward flow of the gas is blocked while, through the effect of buoyancy said gas is forced to leave through the gas outlet hole. Naturally, both of the outlets are on the system vacuum and the gas outlet hole is in direct "air" communication with a buffer bottle, itself being on the system vacuum.

Obviously, the first cavity type is used only in such cases where either there is no gas sensitive particles to flow out with the electrolyte or where no particles flow at all, as is the case where a duct is used as an only control duct which carries no particles at all at any phase of its operation. According to the invention, through the combination of such only control ducts with the only dispenser ducts, i.e, where no gas is generated at all, a very pure particle sorter is obtained, because in such a system, the particles remain in pure electrolyte both before and after processing. Such a system is very useful for the sorting of particles which are very sensitive to contaminations arising from the control gas, which can be some of the live cells.

The second version of the buffer cavity has the advantage of easier operating requirements, which follows from, in this case, that connecting tubes of smaller diameter can be used than for the first cavity type. Although the possibility of a very short contact time between the control gas bubble and the processed particles can not be excluded, this version is also rather useful for the sorting of contamination sensitive particles, such as some of the live cells, because with such a construction, the damaging effect of the gas on the particles is strongly reduced since the contact time between these two entities is reduced to a small fraction of a millisecond, which is indeed a very short time relative to the approximately two hours time during which mouse tumor cells were found to be still alive in an electroyte, bneing contaminated by the by-products of the normal physiological saline water through electrolysis. However, regardless of which one of the two cavities is used, each component of the processed fluid flows through the same multriple tube valve, i.e., one tube for each component.

According to the invention, during the actual processing operation, the suspension of the processed particles flows into the corresponding filtering-collector cavity, where most of the suspension electrolyte is separated from the processed particles, whereby an end suspension of very high density is obtained. This type of cavity is preferably an approximately vertical cylinder of circular cross-section, drilled into the device body where the filtering capillary system, described below, is placed removably into a cartridge-like container, which passes into this cavity in a vacuum tight manner, which is achieved, for example, through a bayonet holder system; this assembly is at the system vacuum since, in the corresponding position of the two position valve, the two cavities are interconnected through tubes of the proper size and length, and since the vacuum is created in the filtering-collector cavity by attching the system vacuum pump through flexible tubes to the outlet of it, where the outlet is situated at the upper part of the cavity; another outlet is situated at the bottom of the cartridge and serves to carry away the filtered waste electrolyte into a waste container, which is also at the system vacuum.

According to the invention, the filtering capillary system functions in the following manner: if the already processed fluid or suspension is to be filtered in order to remove most of its suspending electrolyte, then the suspension, flowing from the corresponding buffer cavity, enters into the filtering-collector cavity through a tube of a suitable diameter in the form of a sequence of small droplets of a few millimeters in diameter and falls at the fine membrane filter, having openings somewhat smaller than the size of the smallest particle to be filtered out of the suspension; the particles in the droplets then are washed away by the following droplets so as to form a ring around that small area of the membrane filter where the droplets fall, forming, in this manner, a crater-like ridge around the point of droplet fall; the diameter of this ridge can be restricted by a ring, which may have the shape of a wedding ring, having a vertical inside wall.

Meanwhile, most of the electrolyte is sucked under through the fine membrane filter by a thicker and softer membrane filter, being similar to a commercial coffee filter and having also a fine enough capillary structure, so that, in this manner, the electrolyte is being sucked further under into a third capillary system, which consits, for example, of a bundle of vertical glass or plasic tubes having inside diameters of about 1.0 mm., and being kept together by one or two rubber bands. From here, the waste electrolyte flows down to the bottom of the cartridge and leaves it through an outlet, being connected by a flexible tube to a waste bottle. After the processing operation, each cartidge is removed from their cavity and the particles are either washed off the fine membrane filter into another fluid of arbitrary volume, or are smeared upon a microscope object glass and then are covered by a thin microscope cover glass for direct observation under a microscope. It is easy to see that the great advantage of the filtering-collector cavity is that during the operation of the system, the processed suspension density is increased to an extremely high degree, saving thereby a considerable amount of time in comparison to the condensation process through centrifugation of the suspension used up to the present time. Furthermore, particles, for example cells in the mitosephase, can be sorted thereby without risking that such cells are damaged by the rough mechanical treatment of them, which may happen in the "open jet" sorter system, where the cells are blown out into the open air and then end up at the surface of a fluid or at the side of the container, whereby they may suffer considerable shocks and structural damage during such impacts.

If the particles are of a very small size, about one micron, then the fine membrane filter might have such small openings that the electrolyle has to be sucked under through the membrane filter by a stronger vacuum system, provided by an auxiliary vacuum pump, used in addition to the system vacuum pump. Otherwise, the filtering-collector system functions in the same manner as is described above, although, in this case, this fine filter should be placed at a metal screen, itself being situated at the top of a cylinder to which the auxiliary pump is connected through a tube; this pump is always having a larger suction effect than the system pump.

Alternatively, and if it is more suitable, then both the two position multiple tube valve, and the filtering-collector cavities are separated from the system, and are placed, separate from each other, outside of the system, where all of the parts are connected to each other through flexible tubes; in this case, the filtering-collector cavities are called filtering-collector bottles. Natuarally, such an arrangement permits the use of larger bottle volumes, which, in some cases, are of some advantage, althopugh the principle of operation and the effectivity of these filtering-collector systems are not changed.

According to the invention, in the combined case, where both pressure at the entrances of the system and vacuum at some of its outlets have to be applied, there the flow control proceeds in accordance with the requirements specified for the two separate cases.

According to the invention, the various construction aspects of the system are as follows: the material of the system is of such quality that it satisfies all the various mechanical, thermal, electrical and optical requirements, defined for the particular system. The embodiment has such an outside structure that an easy attachment of it is possible to the rest of the apparatus into which the system is incorporated. The geometry of the various cavities and ducts of the embodiment not only have the proper shape, but the whole flow system is easily serviceable, which means that any place of it is observable through a stereo microscope of about 50-fold magnification and any part of it is reachable either by a jet of cleaning fluid, such as water, or by a fine thread or wire in order to be able to remove any extraneous pieces from any part of it without being forced to remove some other parts of the system which are otherwise permanently attached to it, where such is the already described thin glass which covers the channels, carved into the surface of the system. If it is necessary, then special cleaning holes are drilled into the system in order to ease such maintenance operations. Naturally, such holes are closed vacuum tight during the operation of the system. The use of a filter, at the entrance of each inlet of the system, reduces the possibility of finding such extraneous material in the flow system. In order to prevent the development of bacteria or alga cultures in the flow system, the walls of the flow system are painted with a proper commercially available epoxy. The development of such cultures are also suppressed if the whole flow system is filled up with alcohol, or by a mixture of alcohol with distilled water, when the system is not in operation.

According to the invention, although the dispenser ducts can branch out into all possible directions, nevertheless, they branch out only with a small angle between them in order to achieve fast dispensing/sorting of the substance or particles by deflecting them only by a very small angle. In accordance with the invention, if the ducts are separated into only dispenser ducts and only control ducts, then the former ones are located close to each other and close to the middle exit duct, which also an only dispenser duct, while the only control ducts surround the former duct types and branch out with a larger angle than the only dispenser ducts. In this manner, an optimum geometry is obtained for both duct types since the only dispenser ducts branch out with a small angle, requiring thereby only a small angle deflection for the subsstance to be dispensed and, consequently, providing fast operation for the device, while the only control ducts, having larger branching angles, create larger deflection of the flow and hence also faster operation, whereby one more optimal geometry is defined for the flow system of this method. If the device is to be combined with and objective of very large opening angle, having also a very short working distance, which is approximately equal to its focus length, then one important requirement for such a device is that the transporting ducts have to be carved into the flat upper surface of the device, preferably together with other ducts, channels and cavities, and whole flow system is covered by the same very thin glass, in order to obtain the required closed, i.e., hole-like, flow system whereby an everywhere closed flow system is obtained; for the very thin glass, a microscope cover glass of about 100 microns is very suitable in most cases. If an optical system is used as a particle analyzer, then the walls of these ducts must be nonreflecting and nonfluorescing black in order to reduce the background illumination to a minimum value.

The apparatus aspects of the invention are as follows: an apparatus used only for the dispensing and/or sorting of the substances, comprises: a suitable variant of the possible dispenser/sorter system; the various containers, attached to its entrances and outlets through flexible or partially flexible tubes; at least one pump, the system pump described earlier, which causes the flow of the substances in the system; and the electronic equipment for monitoring and controlling the dispensing/sorting process. It is clear from the previous description that an apparatus, usable for the sorting of individual particles in accordance with some of their physio-chemical properties, is just as well suitable for some kind of a fluid or gas dispensing process, depending on the construction of the particular flow system since, in the dispensing mode, only the program of the electronic system has to be modified accordingly, while the analyzers, used in the sorting mode, have to be disconnected from the electronic system because the dispensing proceeds always in accordance with a preselected program stored, for instance, in a computer.

In accordance with the invention, if the apparatus is used for the dispensing/sorting of some substances directly into another apparatus, for example, if it is used to inject liquids and/or gases into a combustion engine, then the apparatus of the invention is suitably incorporated into the apparatus to be controlled through the injection process, where several means described above may be unnecessary. For example, the filtering-collector cavities or bottles, and even the buffer cavities might be detached from the apparatus of the invention if other means exist within the apparatus to be controlled which can take over the functions of these means; the two position multiple tube valve, however, has to be retained even in this case for obvious reasons; to lead away the improperly injected substances in the phase of the preadjustment of the apparatus of the invention.

From the previous description follows also that it is possible to construct a large number of various embodiments of the invention, which are different from each other in such aspects as the number of main fluids to be dispensed, or on the substance of these fluids, or they may differ in the nature of the control mediums, or on the number of dispensing and controlling ducts, branching out of the duct branching volume, or whether the system is of the pressure or of the suction type, or if it is the combination of both causes of the flow of the substances inside of it.

BRIEF DESCRIPTION OF THE DRAWINGS

With the above and additional objects and advantages in mind as will hereinafter appear, the present invention will be described with reference to the accompanying drawings, in which.

DESCRIPTION OF THE PREFERRED EMBODIMENTS

Figure 1:
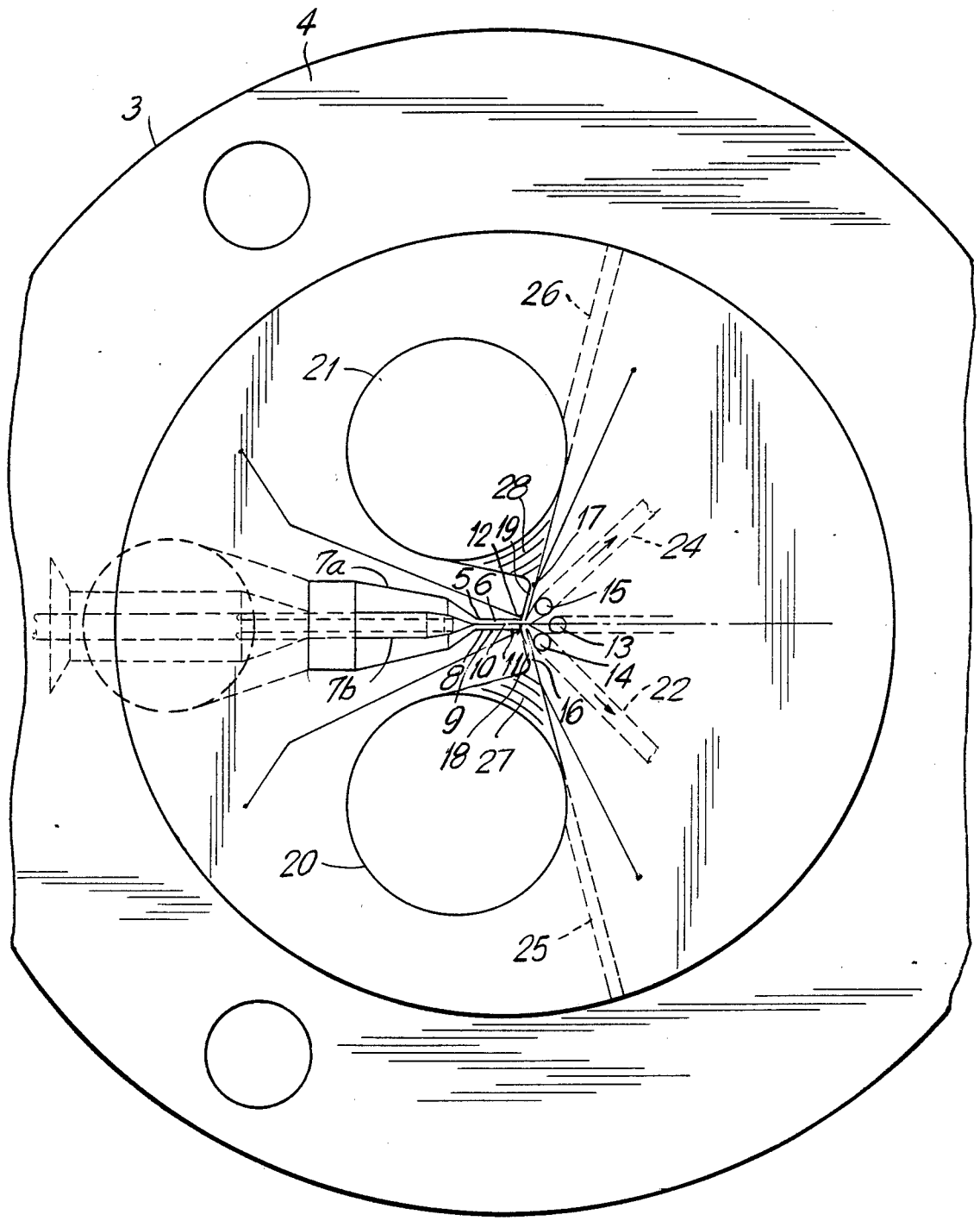
FIG. 1 is a top view of first embodiment of the subject invention.
Figure 2:
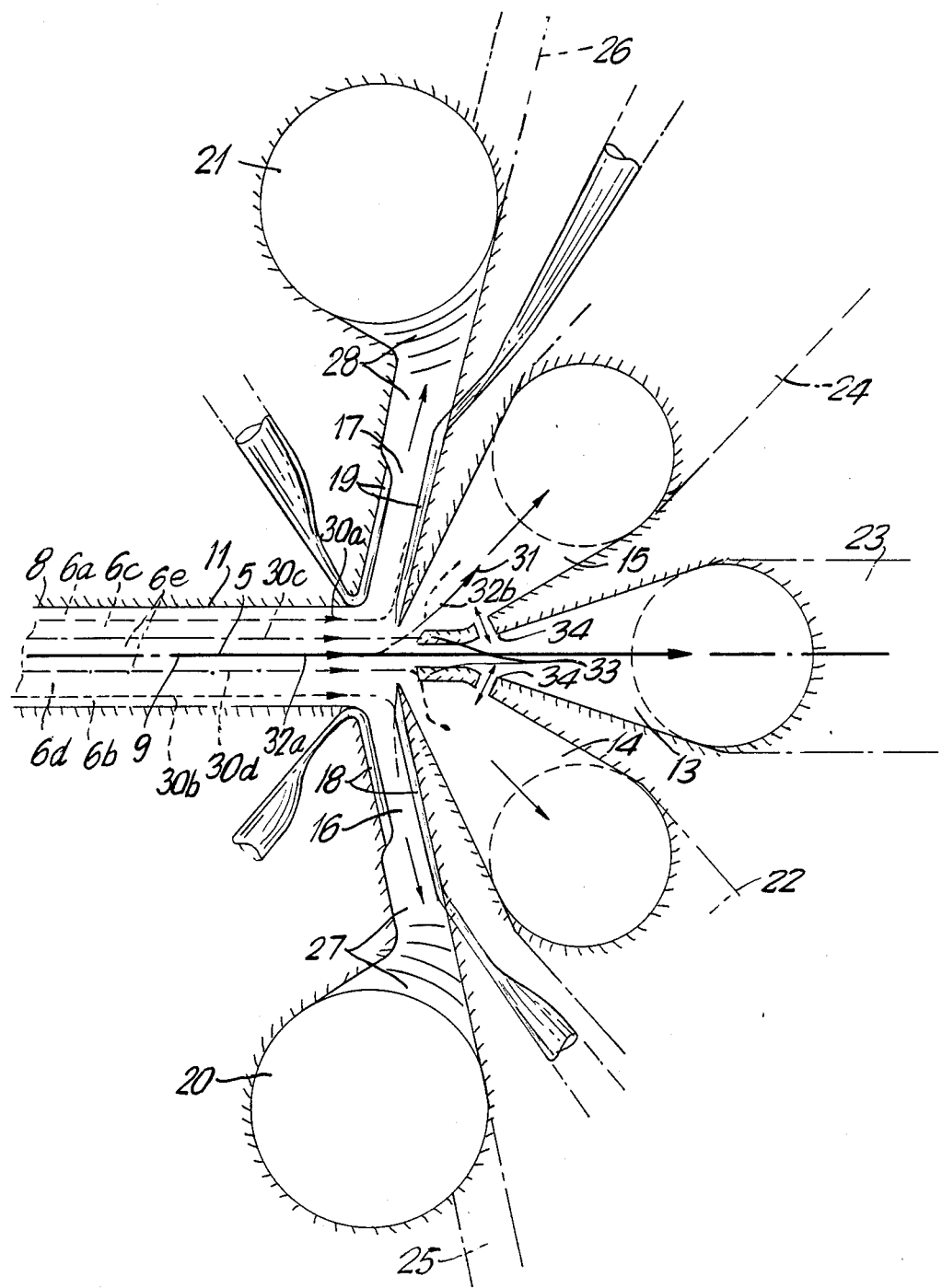
FIG. 2 is a magnified top view of the device in FIG. 1 showing the channel system around the region where the various channels branch out of the channel branching volume.

FIG. 1 shows a top view of a first embodiment of the invention which is known as the "pure electrolyte device" since the particles or cells to be processed thereby remain in a pure electrolyte during the whole time of the processing. FIG. 2 shows an approximately ten times magnified channel system of the first embodiment around the region where the various channels branch out of the transporting channel, which, in this case, is the combination of the connecting channel 8 and the delay channel 11, separated by the orifice 9. Although this embodiment is mainly intended for the clean sorting of contamination sensitive particles, such as some of the live cells, nevertheless, it is clear from its construction that this embodiment can also be used for the dispensing of a fluid or another suspension as well, i.e., it is unable in other moles of operation ref (see. p.56, line 23). In the latter case, the program of the dispensing process is predetermined and carried out by an electronic system, which controls the gas generation between the two electrode pairs, described below. Furthermore, although this embodiment is being presented for a vacuum operation with generated gas as a control medium, as is described hereinafter, it is applicable in a mode of operation where pressure is applied at the inlets thereof.

The body 1 of the device of FIGS. 1 and 2 is of the shape of a double concentric cylinder, having the form of a combination of a larger and a smaller cylindrical disc 2 and 3, respectively. Although the diameter of the larger disc 2 may have any preferred value, that of the smaller disc 3 should be about 18 mm. in order to be able to cover the fine polished top surface 4 thereof with a commericailly available microscope cover glass of the same diameter. This cover glass (not shown) is gliued permanently to the top surface 4 in the normal operation of the device by a nonreflecting and nonfluorescing black glue, such as epoxy, and covers all of the upper, open sides of the various channels and cavities, described below, in such a manner that a completely i.e., hole like, flow-through system is obtained for the whole device. The walls of the channels and cavities are carved in the top surface 4 of the device 1, and are painted with the same black glue, if the device body 1 itself is not made of a material having such optical properties. Furthermore, either the device body 1 is made of an electrically nonconductive material or those parts which carry electrical parts are of the electrically isolating nature.

The combination of the center stream 5, called earlier as the very thin stream, enveloped by the sheath stream 6, is generated in the nozzle chamber 7a where the fluid of the center stream 5, and hence the particles to be processed, flow into the nozzle chamber 7a through the nozzle 7b where the sheath stream 6 fluid envelopes it under the suction effect of a vacuum (system) pump, attached to the outlets of the flow system. The nozzle chamber 7a should preferably be of the type which is described in co-pending U.S. patent application Ser. No. 598,151, filed Apr. 9, 1984, since this chamber is known to produce the stream combination having the characteristics of a very high reliability and stability.

Obviously, the existence of a stream combination of such a quality is the first requirement to obtain a sorter device which has the same very high overall quality as far as its dispensing/sorting operation is concerned. The stream combination 5 and 6 flows through the connecting channel 8, which extends from the outlet of the nozzle chamber 7a to the orifice 9, that is, to the volume of analysis where the main means of the particle analysis, where the optical axis of the UV-microscope objective is situated. Working at the epi-illumination mode, this objective not only illuminates the passing cell or particle with a quasi UV-light, but gathers also the fluorescent light, emitted by the quasi UV-light illuminated particle, in order to be analyzed and subsequently sorted in accordance with one of its properties, such as its volume, DNA or protein content. In other words, if a particle is dyed with one or more special dying substances, then the fluorescent light, emanating from the particle, is proportional to the magnitude of the entity, dyed by the corresponding dying material. The fluorescent light is collected by the very same UV-objective and is converted into electrical impluses in the microscope part of the sorter apparatus as the fluorescent light illuminates the corresponding cathode of one or more photomultipliers. These impluses, in turn, trigger the various electronic equipment, a group of which sets the sorter device into operation. Naturally, the optical axis of the UV-objective does not have to coincide with the center axis 10 of the device body 1. After leaving the orifice 9, the particles pass through the delay channel 11, being still inside of the center stream 5, where the former extends from the orifice 9 to the entrance of the channel branching volume 12, where the latter is defined as the volume delimited by the cross-sections of the six channels which either end or begin there, by the bottom part of the channel system, and by the lower side of the cover glass. After this traversal, and depending on the sorting conditions, the particles either continue their linear flow into the middle dispenser channel 13, where this flow configuration defines also the steady flow state of the suspension and that of the particles too, or they are deflected into one of the side dispensing channels 14 or 15 through the deflecting process, described below. Subsequently, the suspension is filtered either by the inside located filtering/collector cavity (not shown) or by the outside filter/collector bottle of FIG. 5.

The connecting channel 8, introduced for the first time in this specification, is a very important new element since through this channel, having the length of a few millimeters, the hydrodynamical resistance of this part of the system is increased to a maximum, making possible the increase of the system vaccum, i.e., the suction effect, also to the maximum value without causing an unnecessarily large electrolyte flow through the flow system. From the above description, it is clear that through the above geometrical condition, the speed of the operation of this embodiment is also increased.

The increased vaccuum provides several further very important improvements for this shorter type. One of these is the large gas-volume generation for the same amount of gas in moles, as it follows from the gas laws, from where lower electrical power dissipation follows between the gas generating electrode pairs. Furthermore, the contamination of the electrode, if any, caused by the generated gas molecules, is also lower, although in this embodiment, this advantage is not exploited at all since, while channels 16 and 17 are only-control channels, channels 13, 14 and 15 are only-dispenser channels, whereby the gas is completely separated from the particles to be processed in this embodiment of the invention. Additionally, the increased vacuum, the deflection force, acting on the electrolyte elements containing the particles to be deflected, is also increased. Through the use of the delay channel 11, a time delay is provided between the process of particle analysis and the subsequent deflection of this same particle into the preselected only-dispenser channel, if such a deflection is prescribed to take place. This delay is necessary in order to allow time for the device to deflect the center stream 5 into the preselected only-dispenser channel by the time the particle arrives to the channel branching volume 12, i.e., to the end of the delay channel 11. The flow of the electrolyte is purely axial in the delay channel 11, as experiments have shown with older devices, even in that case when the various dispenser channels fan out from the channel branching volume 12 with a somewhat large angle. The fact is due to the inertia of the electrolyte, which the latter has here in the closed channel just as it has it in the open space as it exits at the end of any tube, and this situation makes possible for the center stream 5 to keep its uniform cross-section everywhere as it flows through the flow system of the device at its steady flow state. The channels 13, 14 and 15 are of a purely dispensing nature since control electrodes are not incorporated into any of these channels.

It is important to note that an asymmetrical flow, in the channel branching volume, is the cause of the deflection of the center stream 5 inside of this volume and, hence, the deflection of the particles into one of the only-dispenser channels 14 or 15. Furthermore, it is also clear from the previous description that the asymmetry of the flow is caused at the beginning of the channel branching volume 12 only if one of the only-deflecting channels 16 or 17 does not let electrolyte flow into it for such a long time which is necessary for deflection of the particles into one of the corresponding only-dispenser channels 15 or 14, respectively. Such a paralysis of the flow is caused through the generation of a gas bubble through electrolysis between either of the only-control electrode pairs 19 or 18, whereby the pressure is increased in one of these two channels through the gas generation since in this manner the vacuum is being reduced by the generated gas. Naturally, by properly formed electrodes, vapor could also be generated at the same part of the only-control channels, or by illuminating the same volume between the electrodes by a strong enough laser beam, pressure increase through the generated vapor could also control the dispensing/sorting process.

This process, together with the dynamics of the electrolyte deflection, is defined in great detail in this specification, where the various improvements on the sorting efficiency, in accordance with the invention, relative to those described for the sorter of U.S. Pat. No. 4,175,662, are also described. One of the many important new aspects of the invention, shown in FIG. 1 is that the gas is created only in those channels 16 or 17, into which the particles to be processed never flow. Another related aspect is that in the only-dispenser channels 13, 14 and 15, where the particles flow but gas is not generated and therefore, in this device, the particles remain always in pure electrolyte during and after the whole processing time, from where its name follows. In contradistiction, the possibly contaminated electrolyte, flowing in the only-control channels 16 and 17, leaves the device through the corresponding buffer cavities 20 and 21. The relatively enormous size of these cavities, for the most part being electrolyte free, which can be $10^4$-fold larger than that of the combined volume of all the only-dispenser channels, and only-control channels, and that of the channel branching volume 12, is justified by their function which is to satisfy the various buffering, i.e., compensating functions, described eariler, only if their fluid-free volume is considerably larger than the combined volume of the dispensing flow system. Cleaning holes 25 and 26, which join with these cavities, respectively, are closed air-tight in normal operation, and are opened only when some dirt must be removed through them from the channel branching volume 12 its vicinity. The dispenser channels 13, 14 and 15 may also end in buffer cavities, which can be similar to cavities 20 and 21, if that proves to be necessary, althought thay do not have to each be very large since they are only to compensate the electrolyte fluctuations in the corresponding only-dispenser channels.

The detailed flow and dynamic aspects of the embodiment of FIG. 1 are described below through the use of FIG. 2, which shows the about ten times magnified part of FIG. 1 around the channel branching volume 12, without drawing the buffer cavities at the same scale for obvious drawing technical reasons: they are much too large in comparison to the other parts of the figures. In FIG. 2, the sheath stream 6 of FIG. 1 has been divided, theoretically, into five partial streams in order to make the description of the various processes easier. These partial streams are delimited by the two physically real sides of the transporting channel, which is the combination of the connecting channel 8 and of the delay channel 11, and partly by the virtual planes, imagined to be laid on the stream lines from 30a to 30d and are directed perpendicularly to the bottom of the transporting channel, i.e., to the sheet of the paper of FIG. 2. The extreme side streams 6a and 6b flow into the left and right only-control channels 17 and 16, respectively. The amount of the electrolyte, that flows in these two streams, has to be as large as possible because through these two streams is achieved the generation of the already described asymmetry of the flow in the channel branching volume 12, shown in FIG. 1, and hence, the deflection of the center stream 5, and that of the particles too, into one of the only-dispenser channels 14 or 15. The middle side streams 6c and 6d, delimited by the vertical planes laid on the stream lines 30a and 30c, and 30b and 30d, respectively, flow into the side exit only-dispenser channels 15 and 14, flowing at first against the slightly pointed ends of the separating wall pair 33 and being deflected thereby into these channels. These partial streams are necessary to be used in order to wash the sorted particles into the corresponding filtering/collector bottle, which is located outside of this part of the device and for this reason, is not shown in FIG. 2; since these two streams do not increase the deflection of the center stream 5, therefore, the amount of the electrolyte, flowing in these streams, has to be as small as possible. In contradistinction to the thus far described partial streams of the sheath stream 6 of FIG. 1, the middle partial sheath stream 6e is the only stream having the enveloping nature since only this partial stream envelopes the center stream 5, since the transporting channel is rather wider than deep. Both of these streams enter into the middle only-dispenser channel 13 at the steady state of the flow, or are deflected into one of the only-dispenser channels when the particles are sorted into one of these channels. Since there are only two only-dispenser channels. Therefore, it is possible to sort out only two populations of the particles from their suspension, the remaining third part of the latter is called residue.

The deflection process, i.e., the deflection of the center stream 5 and, hence, that of the particles, into the left only-dispenser channel 15, which is being continued by the left outlet hole 24, in detail, is as follows. Since the device, shown in FIGS. 1 and 2, is of the suction type, therefore, the flow of the electrolyte is controlled by the generation of gas through electrolysis, or by another appropriate vapor producing process described earlier. As it is well known, such gas is generated by sending a well controlled electrical current impulse through the electrolyte, flowing between the electrode pair 18, itself being imbedded in the vertical walls of the right only-control channel 16. It is easy to see, furthermore, that of the rate if the gas-volume production, which is not equal to the gas molecule production in males, between the electrode pair is not smaller than the rate of the flow of the electrolyte in the right only-control channel 16, or in its lower part 27, then the electrolyte flows undisturbed at the down stream end of the gas bubble towards the buffer cavity 20 since the generated gas fills up the volume being left empty by the electrolyte at the same rate the electrolyte flows out therefrom. This is naturally possible since during this process the pressure has been increased between the electrode pair to such a value and for such a long time that no further electrolyte flow into this only-control channel is possible during this time. This is in accordance the invention which says that during gas production, the pressure has to be increased, i.e., the vacuum has to be decreased, to such a value that no electrolyte is able to enter into this channel. From this floows, therefore, that during gas production no suction is exerted on the electrolyte at the up-stream end of the electrode pair 18, i.e., at the inlet of channel 16. In other words, at said rate of gas generation between this electrode pair, the right only-control channel 16 is overflown by the gas or vapor, to such an extent that at the constant vacuum, exerted at the low-stream end of channel 16, i.e., in part 27 of this channel, only the generated gas bubble and the electrolyte at the low-stream end of the former is sucked towards the right buffer cavity 20 and, therefore, there is no more suction effect left to deflect the right extreme side stream 6b into the only-control channel 16. Consequently, the symmetrical flow, which exists in the transporting channel at the steady flow state, is thereby destroyed since the otherwise powerful right only-control channel 16 is now being paralyzed in the manner described above. The consequence of this paralysis is that the left only-control channel 17 and the left only-dispenser channel 15 suck in more electrolyte than they do at the steady flow state since their capability to deflect the various partial streams is now not compensated by the right only-control channel 16. The result of this is that the right extreme side stream 6b flows now partly into the right only-dispenser channel 14 and partly also into the middle only-dispenser channel 13. Additionally, the also deflected right middle side stream 6d flows into the middle only-dispenser channel 13, and further in the middle outlet hole 23, and the middle partial sheath stream 6e, together with the center stream 5 flow into the left only-dispenser channel 15, and into the corresponding outlet hole 24, if the deflected amount of the electrolyte of the right extreme side stream 6b is large enough. Consequently, an excess flow of the electrolyte takes place both in the middle side stream 6c and in the left extreme side stream 6a.

At this phase of the deflection process, the center stream 5 takes its "to-the-left-deflected" form, as is indicated by curve 31, and if a particle is located slightly at the up-stream side of the only-control channels 16 and 17, i.e., at the position 32a, and if the center stream deflection time is long enough, then said particle or cell enters into the left only-dispenser channel 15, as is indicated by the point 32b. The return to the steady flow state phase starts at the ceasing of the gas generation in the only-control channel 16 between the right electrode pair 18, i.e. timewise speaking, at the end of the electrical impulse. Consequently, the generated gas bubble is sucked out of channel 16 into the right buffer cavity 20, and the force, exerted at the right extreme side stream 6b at the steady state, is acting on it again when this stream starts to flow into channel 16 again. After this process, all the streams return to their steady state flow since the symmetry of the pressure has been restored everywhere, whereby the sorting of the particle 32a into the left only-dispenser channel 15 has been completed; after this process, the particles leave the device through the left outlet hole 24. It is easy to see that the sorting of a particle into the right only-dispenser channel 14, follows in a similar manner if a gas bubble is generated in the left only-control channel 17 between the electrode pair 19. In this case, after being deflected into the right only-dispenser channel 14, the particles leave the device through the right outlet hole 22 and enter into the corresponding filtering/collector bottle (not shown).

The process of dispensing, and hence that of the particle sorting, is obviously a series of partial dynamic processes, which consist of a series of irregularly following accelerations and decelerations of the fluid substances in the various channels and in the channel branching volume 12, as the particles to be sorted follow each other in a random manner. Therefore, for high speed operation of the device, it is necessary that the force-to-mass ratio, involved in this process, be as large as possible. Additionally, in this case, the suction effect, i.e., the vacuum acting on the flow system, has to be as high and as constant as possible during the whole operation of the system regardless of what type of dispensing phase exists in the system. Furthermore, the fluctuating amount of the electrolyte also has to be as small as possible, and the deflection of the particle into one of the side-only dispenser channels 14 or 15, at the smallest angle of the deflection from its steady state flow line, defined earlier. From which follows, obviously, that these channels are to be manufactured into the upper surface of the device 4 of FIG. 1, at the smallest possible angle, measured from the steady state flow line. Furthermore, in order to keep the flow-through of the electrolyte at a low value in spite of the high vacuum applied at the system, i.e., at about a velocity of 10 m/sec., the connecting channel 8, shown in FIG. 1, has to be as long and its cross-section as small as possible in order to increase the hydrodynamic resistance of this channel to the maximum possible value for a given device. Only in this manner, is exerted an optimum force at the electrolyte high asymmetry in its flow if one of the only-control channels, i.e., either 16 or 17, is paralyzed through gas generation in one of these channels to such in electrolyte, as well described above.

Furthermore, the suction stabilization is achieved through the use of the buffer cavities, which are large holes 20 and 21, drilled into the body 1 of the device quasi perpendicularly into its top surface 4, as shown in FIGS. 1 and 2, and most of their volume is free of an electrolyte, from where their stabilization characteristic follows. Their outlet holes are connected through flexible tubes (not shown) to a waste bottle of very large volume in such a manner that both the electrolyte and the generated gas can flow parallel to each other without blocking each other's flow into the bottle. On the other hand, the outlet holes of the only-dispenser channels 13, 14 and 15 are connected through flexible tubes to the filtering/collector bottles of very large volume where the already processed suspension is filtered, after flowing through the two-position multiple-tube valve, which, in this case, is a triple-tube valve.

The filtering/collector bottles, described in more detail below, are under the same vacuum as the buffer cavities, and are positioned under the device in such a manner that the processed suspension, flowing out of the buffer cavities, flows not only under the effect of the vacuum but also under the effect of gravity, an appreciably large force here. Naturally, the same is true for the fluid flowing out of the buffer cavities connected to the end of each of the only-control channels 16 and 17, although, while for these latter channels, buffer cavities are necessary in order to compensate both the vacuum and the influx fluctuations and in order to detach the latter fluctuation from the large mass of the slowly flowing already processed electrolyte of the connecting tubes, for the only-dispenser channels 13, 14 and 15, such buffer cavities are only then necessary if the electrolyte fluctuations in these channels are much too large so that the speed of the operation of the device would be reduced without such cavities. Additional compensation of the suspension fluctuation in the only-dispenser channels is also obtained through the small channels 34 if they are at such a position that they permit a small communication of the fluid between the two side channels with the middle outlet channel without letting the sorted particle to flow erroneously into this latter channel; for smaller electrolyte fluctuations, these compensating channel pair 34 can be sufficient.

The buffer cavities, therefore, are very important elements of the new device, and of the invention too, and their necessity was clearly seen after the analysis of the performance of the previous sorter devices, constructed in accordance with U.S. Pat. No. 4,175,662, which naturally does not describe such a cavity since it was not known at that time. In the previously conducted experiments, it was observed that by generating gas bubbles only in one of the side channels, using an impulse generator to provide the electrical current impuses for the gas generation, the center stream, made visible and therefore distinguishable from the sheath stream by using a thick suspension of dyed mouse tymus cells of about 5 microns diameter, have shown a steady deflection away from that side channel where the gas bubbles were generated. This observation shows clearly that without the vacuum compensating effect of the buffer cavities, the vacuum decreases for increasing gas bubble production in the control channels, i.e., in those channels where gas is produced, and this is one of the justifications for the use of these cavities described below. High quality sorting of cells was, however, possible in the older devices when the number of cells to be sorted was about the same in both populations. However, in the asymmetrical sortings, i.e., where the cell number was considerably different in the two cell populations, only the sorting of the larger cell (number) component was good enough. This only partially successful sorting can be explained in such a manner that, due to the device configuration, the relatively small amount of gas, forced to stay at the channel-end, i.e., where the latter goes over to a quasi vertical hole, through the effect of buoyancy acting on the gas, could not completely stabilize the vacuum fluctuation and, as a consequence, an average deflection of the center stream came into existence, which favored the sorting of the larger number component cells and forced the cells of the other component to slide along the wall of the entrance of the corresponding dispenser channel since the deflection for these cells was not large enough to prevent them from sliding on the wall, and as a consequence, usually most of these cells were destroyed and recovered only in the form of debris.

It is important to note that buffer devices are often applied at other branches of the modern techniques, too. For instance, the storage elements, at the interface between the central processing unit of a computer and the attached peripheral unit, such as a keyboard, are a build-screen, functions in the same manner by permitting fast operation of the extremely fast central processing unit in spite of the quoted slowly functioning peripheral units. From the above description, it is also clear that for fast and reliable sorting, as is defined above, the use of the buffer cavities are of paramount importance both for the stabilization of the vacuum and for the decoupling of the very fast fluctuating suspension to be dispensed in the dispenser channels from the very slowly flowing, and the large amount of the processed substance of the connecting tubes.

The fact that in these cavities the gas is also separated from the suspension, as the result of the known buoyancy, provides yet a third use of these cavities; this third type of cavities are used, however, only in such devices where the control and dispensing process takes place in the same channel or duct.

Since the mass of the suspension, shaked during the dispensing phase, is to be of the minimum amount, therefore, the cross-section of the various channels of the dispenser part has to be as small as possible, i.e., the transporting channel, which is the combination of the connecting and the delay channels 8 and 11, respectively, has to be rather wider than deep, if a large deflection of the center stream 5 is to be caused only in the horizontal plane, and this channel combination has to be as long as possible. The width and depth of the transporting channel is restricted, however, also by the type of the UV-objective, which is used for most of the optical analysis of the particles and is positioned at the point of observation 9, also called the orifice, where this objective has to be able to "see" the particles, flowing inside of the center stream 5, without any optical hindrances such as the vertical walls of the channel. Intermittent motion of any amount of the suspension, not enclosing the particle to be deflected, has to be also of the minimum amount in these channels, in accordance with the invention, since the back-and-forth shaking of this electrolyte implies the slowing down and then the accelerating of this amount of the electrolyte, which is a time consuming process, and causes a reduction of the speed of operation of the device.

Therefore, the electrode pairs of the only-control channels 16 and 17 have to begin as close to the entrance of these channels as possible, although care should be taken to avoid the spilling of the control gas into the channels which are located down-stream from the entrance of these only-control channels, because such an overspilling of the gas might cause some undesirable contamination of the originally clean electrolyte flowing in the delay channel, which is the basic characteristic of this type of sorter/dispenser device. As was defined earlier, the length of the only-dispensser channels has to be at least so long that the control medium, in this case a gas, can develop in it without flowing into the corresponding buffer cavity; otherwise its development and consequently, the deflection process could be distrubed.

The angle of the deflection of the center stream 5 from its steady flow state has also to be as small as possible in order to obtain a short deflection time and, consequently, a high speed of operation for the device. This angle is reduced mainly by reducing the thickness of the entrance walls 33 of the middle only-dispenser channel 13. Using materials such as mylar, the thickness of these walls can be reduced to about 10 to 20 microns, reducing thereby the angle of deflection of the center stream 5 the about 30°, or even smaller, which is an appreciable improvement relative to the 70° of the older devices.

In general, the body of the device is to be made flat and its diameters as small as possible, so that the various inlet and outlet channels or holes, and the cleaning holes 25 and 26 can also be made short; the exit holes 22, 23 and 24 are drilled into the device body with a small grazing angle, abut 30°, relative to the top surface 4 of the device, and the holes are to join the corresponding only-dispenser channels 14, 13 and 15 smoothly, so that through these holes, the branching volume 12 can also be reached easily with a thin and flexible thread or metal wire to clean out this part of the flow system without removing the cover glass, which covers the whole flow system, the latter being carved into the top surface 4 of the device. This easy way of cleaning the channels is indeed a great advantage of the new device, because, as was found in previous works, the removal and the subsequent replacement of this glass is a rather redious and time consuming work which requires considerable concentration during the replacement thereof. Since, for the particle analyzer, an optical type is used, the device is either made of nonreflecting and nonfluorescing material, or all of the channels have to be covered by a thin sheet of such a material in order to reduce the undesirable background illumination to a very small value. Actually, even the cover glass is glued to the top surface 4 with such a material for the same reasons. Obviously, the sensitivity of the optical analyzer is considerably reduced by a strong background illumination. The body of the device, furthermore, should be made of an electrically nonconductive material since electrical wires are embedded into it, which sometimes carry a voltage of several hundred volts.

Finally it is easy to see that the embodiment of FIGS. 1 and 2 can be used even in the pressure mode, where higher than atmospheric pressures are applied to the containers, connected to the inlets. In this case, however, the control medium, a fluid or gas, is applied on the only-control channels 16 or 17 through the buffer cavities 20 and 21, the diameter of which is much smaller in this case since no buffering takes place in these holes in this mode of operation. Buffer cavities, however, might be necessary in the only-dispenser channels 13, 14 and 15, if they are needed at all; the small connecting channels 34 are useful in this case definitely.

Figure 3:
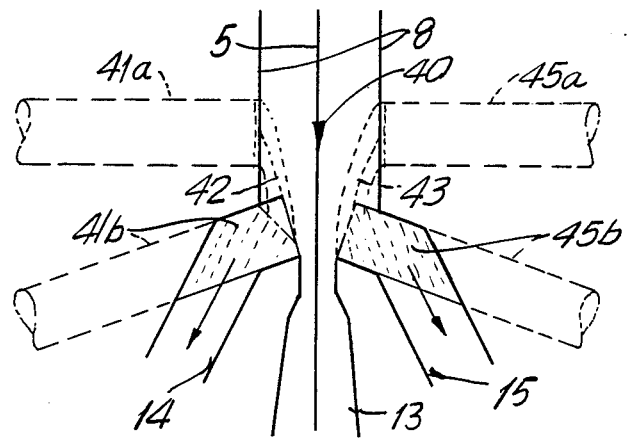
FIG. 3 shows a top view of a second embodiment of the channel system with different electrode geometries.
Figure 4:
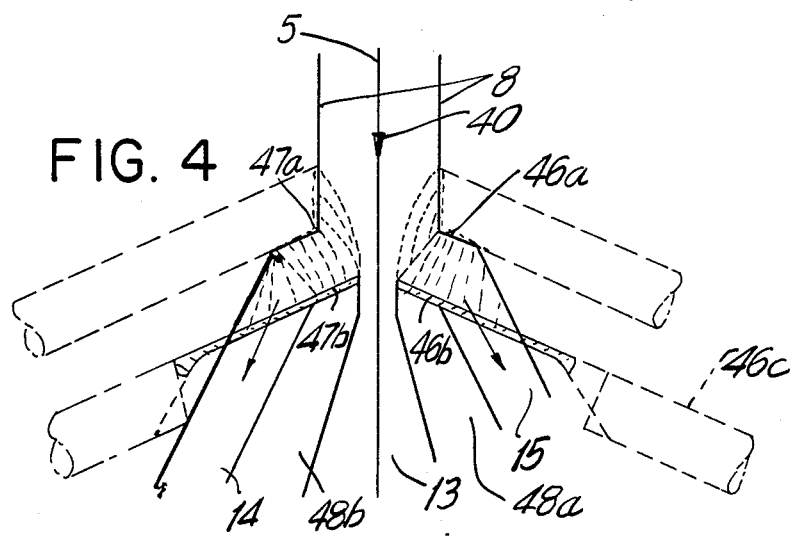
FIG. 4 shows a top view of a third embodiment of the channel system with a still different electrode geometries.

FIGS. 3 and 4 show two other practical arrangements for the control electrodes, which are inbedded in the device body in such a manner that the control gas is generated partly inside and partly at the very vicinity of the channel branching volume, defined here by the joining of the transport channel 8 and the three dispensing contorl channels 13, 14 and 15, which are called in this manner since they carry out both types of operation; the cover glass is not shown in these figures in order to simplify the drawings. In accordance with the invention, these types of electrode arrangements are the optimal ones for the operation of such types of devices, i.e., where the same outlet channels carry out both the flow control and the dispensing operations. Accordingly, the deflection of the center stream 5 is caused to the left, relative to its steady flow state line 40, through the generation of gas between the electrode pair 41a and 41b when an electrical field 42, shown by discontinuous curves, and the concommittant electrical current, is created between the electrodes. In the same manner, deflection of the center stream is caused to its right, if the electric field 43 is generated between the electrode pairs 45a and 45b. It is clearly seen from FIG. 3 that the active surfaces of the electrodes 41a and 45a are mostly only their tips, with which they form a part of the walls of the transporting channel 8. On the other hand, the active surfaces of the electrodes 41b and 45b, i.e., the shaded areas, form a part of the bottom of the dispenser channels 14 and 15 at the channel branching volume. Consequently, the gas generation takes place, off-center, partly at the inside of the channel branching volume and partly in the channels. Since the electrode tips of 41a and 45a can be made of the pointed form, therefore, this electrode arrangement can also be used readily for the generation of well controlled electrical arcs, described earlier as other means for the generation of the control medium, i.e., of the control vapor.

For the electrode geometry of FIG. 4, the control electrodes 46a and 46b are so constructed that these electrodes are closer to each other than those of FIG. 3, and they also have larger parallel surfaces and, consequently, a larger amount of gas or vapor can be generated between these electrodes than with those of FIG. 3. The construction conditions are here somewhat more difficult since the low stream electrode 46b forms a part of the channel separating wall 48a and it has to be cut in such a manner that it does not close the dispenser channel 15, that is, the active part of the electrode 46b is connected to the main connecting wire 46c by a part of this electrode which lies deeper than the bottom of channel 15. Although the construction of such an electrode geometry is not very difficult, nevertheless, it demands some additional work, relative to that of FIG. 3. The right hand side of the flow system, and all the aspects related to it, are similar to those of the left hand side. Electrical arc generation is also easy here since electrodes 46a and 47a have sharp edges towards their counter part electrodes and such sharp edges facilitate easily the generation of such an electrical phenomenon.

Figure 5:
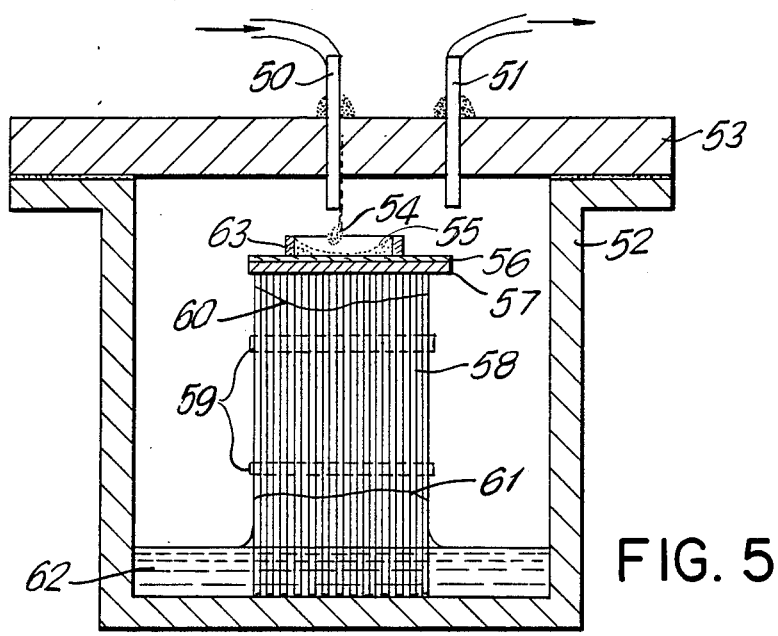
FIG. 5 shows a cross-sectional view of a filtering-/collector bottle, to which the filtering/collector cavity is very similar, together with the capillary filter system.

FIG. 5 shows the vertical cross-section of the filtering/collector bottle, described earlier as an alternative to the filtering/collector cavity, having, therefore, the same inside structure of this type of bottle, where both devices serve for the separation of the already processed particles, such as cells, chromosomes, etc., from most of their suspending electrolyte, whereby an almost arbitrarily thick suspension is obtained, since this gentle filtering process separates almost all of the electrolyte from the particles.

The operation of the filtering/collector bottle is as follows: the influx tube 50 of the bottle is conected by a flexible tube, through the multiple-tube two-position valve, which, in this case, is a triple-tube valve having one tube for each outlet of the device, to the corresponding exit holes of the dispenser/sorter device; in turn, each of the bottles are connected through their air exit tubes 51 to a vacuum system, which suck the various fluids through the whole flow system of the device. Consequently, the electrolyte enters into the bottle through the influx tube 50 in the form of droplets 54 into the volume, defined by the container part 52 and the air-tight cover piece 53, where some of the droplets carry particles within themselves; a particle is indicated by a point in the droplet 54. Gas, however, does not enter into this cavity since it has been already separated by one of the two methods described earlier. While the particles are distributed in the small ridge 55 of the form of "an extinct crater" on the fine filter 56, the fluid itself is sucked under by the surface tension of the capillary system of this filter, having openings larger than one micron but definitely not larger than the smallest particle to be filtered out of the suspension. The electrolyte then is sucked further under into a thicker filter 57, from where it is sucked further down to the bottom of the container by a vertical capillary system 58; the paper filler 57 can be of the same kind as an ordinary coffee filter and the vertical capillary system 58 can be a bundle of thin glass tubes of about 2 mm. diameter, in which case, the bundle has to be kept together by at least two rubber bands 59. The diameter of the particle ridge 55 on the fine filter 56 can be delimited by a small ring 63, the diameter of which must be so large that there always remains a small part free on the filter 56 which the particles do not occupy around the point where the droplet 54 falls; only in such a condition is the filter 56 able to suck the electrolyte downwards and away from the particles left on the ridge 55; in the opposite case, these particles could clog up the fine filter, causing an overflowing of the ridge with electrolyte and washing away the particles into the normally particle free waste electrolyte 62, collected at the bottom of the bottle 52. Naturally, these particles are lost for any further use. The quasi vertical capillary system 58 can also be made of very small beads, being kept together by a shell of a cylindrical form and having a large number of openings at its vertical side. The filtered suspension fluid forms a "hanging-capillary-water form" 60, from where the electrolyte drops to the normal capillary level 61, and from where it again flows down to the already filtered electrolyte 62. Obviously, it is a very important condition for the correct operation of this filtering system that the "hanging-capillary-water" 60 never gets into a permanent contact with the normal capillary level 61 of the already filtered electrolyte because in this case, the two fluids would form a steady fluid between the normal level 61 and the paper filter 57 and instead of a suction downwards, a suction upwards can take place with the obvious adverse effect on the particle filtering process in this bottle.

After sorting, the particles 55 of the ridge, collected on the fine filter 56, are either washed off into another fluid, or are smeared at a microscope object holding place for direct visual observation and study. Depending on the amount of the new fluid, in this manner an arbitrarily thick new suspension of the processed particles is obtained. The area of the fine filter 56 is not smaller than it is necessary to collect all the particles, which means that the particle carrying suspension must not flow off on its edges but it must flow through the fine filter itself.

It is possible to sort the processed particles directly at an object holder glass if this is placed right under the influx tube 50 with a small angle to the horizontal and if additionally, a screen filter of the proper opening size is placed on the glass. In this case, while the electrolyte is let flow under the screen filter and between its holes off the glass, the particles are retained between the openings of the screen filter; therefore, the openings must be larger than the particle size.

For the particles of the size of the order of one micron, a smaller than one micron fine membrane filter 56 is required in order to sort these particles on this membrane filter, and from direct experiences, is obtained that for such filters the capillary suction system is not strong enough. Therefore, in this case, the vertical capillary system 58 is replaced by another stronger vacuum system, which is a vertical cylinder with a strong grid-like holder at the top side thereof, as supporting system for the fine and thick filters. Inside of this cylinder, such a high vacuum is created by an auxiliary vacuum pump which is able to suck the suspending electrolyte through the two filters, laid upon each other and then upon the grid-like structure, and where the procesed particles can be recovered from the fine filter in the same manner, as is described for the former version.

From the above description, it follows clearly that, in both versions of the sorting on membrane filters, and at the object holder glass, the filtering and hence the condensing process of the particle suspension is a very gentle one, since in these systems, the particles fall gently and together with a large amount of electrolyte from the height of one or two centimeters at the membrane filter or object holder glass, from where they are recovered in an also very gentle manner, for further use, instead of being blown out with a very high velocity in a stream jet of the electrolyte and arriving often at the sides of the container, as is the case of the jet method. Therefore, the filtering/collector cavity, and/or the filtering/collector cavitoy, and/or the filtering/collector bottle are additionally very suitable for the structural study of cells in their mitose-phase, or for the study of chromosomes, and in general, in any "structurally sensitive" case.

Numerous alterations of the structure herein disclosed will suggest themselves to those skilled in the art. However it is to be understood that the present description is for purposes of illustration only and not to be construed as a limitation of the subject invention. All such modifications which do not depart from the spirit of the invention are intended to be included within the scope of the appended claims.

What is claimed is:

1. A method for fast and reliable control of the flow of fluid substances and fluid volume elements carrying individual particles of a suspension, flowing in a hole-like, environmentally friendly, duct flow system having inlets and outlets, under the effect of pressure differential existing between the inlets and outlets of the system, the duct flow system having one mode of operation in which control of the flow of the fluids is used for dispensing the fluid substances through a number of outlets of the system with a preselected dispensing format, and a second mode of operation in which control of the flow of the fluid substance is used for dispensing volume elements, containing at least one particle, in accordance with at least one individual physio-chemical property of the particles, so as to sort these particles out of their original suspension into a plurality of partial suspensions, and where a combined multi-parameter compensating process assures fast and reliable achievement of each of a number of preselected flow configurations, defined by the distribution of the flow of the substance in the various outlets of the system, whereby through said compensating process, each of the flow configurations is achieved independently from the other flow configurations during the whole operation of the system, wherein said method comprises the steps of:

(a) transporting said fluid substances in at least one transporting duct towards a duct branching zone [while analyzing the individual particles in the ducts, in the second mode, in accordance with at least one of their properties], and subsequently determining a flow configuration of the substance in the various outlets of the flow system [while, in the first mode, the flow configuration is determined without analyzing the particles] when said system is in said first mode without analyzing said particles, and when in said second mode analyzing for at least one of their properties;

(b) creating a corresponding flow configuration for said duct branching zone, where not only at least one transporting duct enters but also a multitude of dispensing ducts branch out radially in space, by discontinuously injecting a fluid control medium, at the entrance of a number of dispensing ducts of the multitude of dispensing ducts where the substances to be dispensed are not to enter, with a force and at a place of injection so that the substances are forced to enter into other dispensing ducts of the multitude of dispensing ducts, while the control medium flows into that duct into which it was injected, the discontinuous injecting causing a small mass of the control medium and the substances to rapidly fluctuate;

(c) providing a buffer cavity at the end of each dispensing duct;

(d) transporting the dispensed substances in their dispensing ducts toward respective corresponding buffer cavities, and transporting the control medium in its ducts towards buffer cavities corresponding to the control medium ducts;

(e) decoupling the rapidly fluctuating small mass of the substances and the control medium, flowing from the dispensing ducts into the corresponding buffer cavities, from the fluid flowing in the dispensing ducts, which is of a larger mass or amount which slowly out of the buffer cavities since each of these cavities has a fluid-free volume which is substantially larger than that of the whole duct flow system, whereby a very fast fluctuation of the small amount of the substances to be dispensed is possible and from where the very fast operation of the system also follows;

(f) buffering, simultaneously in the buffer cavities, the pressure, which is caused partly by a fluctuating influx of the control medium into these cavities, and selectably separating the control medium from the processed substance when the control medium is of a gaseous nature and the processed substance is of a liquid nature by forcing the gaseous control medium, through the effect of buoyancy, to leave the cavities through a gas outlet hole, situated at the upper part of the cavity, and simultaneously letting the dispensed substance leave the cavity through an outlet hole, situated at the bottom of the cavity, and causing, through this type of buffering, the exact return of the pressure and flow conditions in the dispensing part of the system to a steady flow state where no control medium is injected, whereafter, the system is ready for another prescribed and completely independent dispensing phase; and (g) directing the dispensed fluids through a two-position multiple-tube value selectively leading to corresponding filtering/collector means for separating the sorted particles from most of the suspending fluid, so that a very highly concentrated suspension is obtained, and into a waste container, the obtained end result then being transferred manually to other containers.

2. The method according to claim 1, wherein the pressure difference causing the flow in the system, is created by applying a higher than atmospheric pessure at the inlets of the system, while the outlets of the system remain at atmospheric pressure.

3. The method according to claim 1, wherein the pressure difference causing the flow in the system, is created by applying a vacuum at the outlets of the system, while the inlets of the system remain at atmospheric pressure.

4. The method according to claim 1, wherein the pressure difference causing the flow in the system, is created by applying a higher than atmospheric pressure at the inlets of the system, and applying a vacuum at some of the outlets of the system, the remaining outlets being left at some other pressure.

5. The method according to claim 1, wherein the fluid substance occupies the whole crosssection of some of the transporting ducts and in other transporting ducts the flow geometry is of another form, the transporting ducts being entrance ducts of the flow system.

6. The method according to claim 1, wherein more than one substance occupies some of the transporting ducts, which substances flow quasi-laminarly beside each other in each of the ducts, said quasi-laminar flows being arranged in a flow chamber attached to the entrance of each of the transporting ducts.

7. The method according to claim 1, wherein at least one thin stream flows in some of the transporting ducts, this at least one stream being enveloped by a sheath stream which keeps the thin stream at a stable position as it flows in the transport duct, said flow being created in a nozzle chamber.

8. The method according to claim 7, wherein said thin streams, in a steady flow state, flow into the same dispenser duct while in the dispensing phase, they flow into the preselected dispenser ducts.

9. The method according to claim 7, wherein said streams have a cross-section so as to orient the particles, carried by said streams, into a proper direction relative to the cross-section of the corresponding transporting duct so as to obtain optimal analyzing conditions for the particles.

10. The method according to claim 1, wherein places of particle analysis are only located at a distance from the entrance of the duct branching zone so that the flow-through time of a particle between these two places is not shorter than the time necessary to establish the predetermined dispensing flow configuration for sorting of the particles.

11. The method according to claim 3, wherein the transporting channels have a hydrodynamic resistance which is as large as possible.

12. The method according to claim 1, wherein the control medium is injected into the entrance of the duct at an optimal place so that the amount of the substance to be processed has a minimum value that has to be redirected during establishment of the required flow configuration, the place of the injection being slightly inside of the duct branching zone and partly in the corresponding dispenser duct.

13. The method according to claim 12, wherein the control medium is injected into said optimal place through a control hole which communicates with the outside of the system.

14. The method according to claim 12, wherein the control medium is a vapor or gas.

15. The method according to claim 1, wherein the dispenser ducts have a minimum length so that the control medium does not reach the end of these ducts during its injection therein, so that dispensing is not disturbed by a possible pressure varation caused by the entrance of the control medium into the corresponding buffering cavity.

16. A dispensing and sorting device for a fast and reliable control of a flow of fluid substances and volume elements containing individual particles in suspension, in a closed, hole-like, environmentally friendly, duct system having inlets and outlets under the effect of a pressure difference, existing between the inlets and the outlets, the control of the flow, in a dispensing mode, being useable for dispensing the fluid substances through a plurality of outlets of the duct system in accordance with a preselected dispensing format, or in a particle sorting mode, for dispensing volume elements of the suspension, containing at least one particle, in accordance with at least one individual physio-chemical property of the particles, so as to sort these particles out of their original suspension into a number of groups, and where a combined compensating process assures not only a fast and reliable achievement of each individual, preselected flow configuration, differing from other flow configurations in that aspect in which dispenser ducts the just dispensed substance flows, but also a fast and exact return of the flow to its steady state flow configuration after each such dispensing phase during the whole operation of the system, whereby one dispensing or sorting phase is completely independent from all the preceeding phases and the fast fluctuating dispensing flow system is decoupled from the slowly flowing, already processed dispensing from tubes connected to the device, said device comprising:
  (a) at least one transporting duct having a downstream end and which carries not only the fluid substance towards a duct branching zone, but also contains apparatus for analysis of the particles to be analyzed in the particle sorting mode;
  (b) at least one duct branching zone which is delimited approximately by the downstream ends of the transporting ducts and entrances of dispensing duct branching out from this zone;
  (c) at least one device causing an increase of the fluid pressure at the entrances of the dispensing ducts through injection of a control medium so that by increasing the pressure at one such duct, the substance, or the particle carried in it, is prevented from entering into this duct but is constrained to enter into such a duct whee, during the same dispensing phase, such a pressure increase does not take place, during the injection, it is the control medium that flows into that duct where this medium is being injected;
  (d) at least two dispensing ducts, branching out of the duct branching zone at a small angle relative to each other;
  (e) a corresponding buffer cavity at the end of each dispensing duct having a fluid-free volume which is substantially largr than taht of the combined flow system, which consists of all the transporting ducts, the duct branching volume and all the dispensing ducts, so as to compensate for pressure fluctuation and to decouple a rapid fluctuation flow of the fluid in the dispensing ducts from a large amount of the already processed fluid, flowing out of the device slowly and without any appreciable fluctuation;
  (f) a two-position multiple-tube valve to direct, at one position, the various processed fluids into other containers, and in the other position, to direct all the fluids into a waste container; and
  (g) filtering/collector cavity means connected to the one position of the valve, for selectively increasifng the concentration of the particle suspension after processing so that most of the suspension is separted from the particles.

17. The device according to claim 16, wherein the various substances flow under the effect of pressure applied at the containers of the substances, while the outlets of the device are at atmospheric pressure.

18. The device according to claim 16, wherein the various substances flow under the effect of a vacuum applied at the outlets of the device, while the inlets of the device are at atmospheric pressure.

19. The device according to claim 16, wherein the various substances flow under the effect of pressure applied at the containers of all the substances flowing in the device, while at least some of the outlets of the device are at a vacuum and the remaining outlets are at an arbitrary pressure lower than the pressure applied at the containers.

20. The device according to claim 16, wherein more than one transporting duct is provided, each of the transporting ducts carrying only one type of substance towards the duct branching zone independently from the other transporting ducts.

21. The device according to claim 16, wherein more than one transporting duct is provided, each of the transporting ducts carrying more than one type of fluid substance towards the duct branching zone independently from the other transporting ducts.

22. The device according to claim 16, wherein any of the transporting ducts carry at least one thin stream having a cross-section which is very small relative to that of the duct, the at least one stream being enveloped by at least one kind of fluid subtance as it flows toward the duct branching zone without turbulence.

23. The device according to claim 22, wherein said thin streams have a cross-section geometry that provides a preferred orientation for processing the particles carried by these individual streams.

24. The device according to claim 16, wherein a transporting duct accommodates one of at least one particle analyzing device, and at least parts of such a device for converting an amount of at least one preselected physio-chemical property of the particles into electrical impulses to be processed electronically be connected electronic equipment.

25. The device according to claim 16 or 18, wherein the transporting ducts have a maximal hydrodynamical resistance so as to allow application of as high a vacuum at the outlets of the system as possible.

26. The device according to claim 24, wherein said particle analyzing devices, or parts of them, are only as close to the duct branching zone so that the particles flow-through time between these two places is not shorter than a time which is required to generate the preselected dispensing flow configuration in the duct branching zone.

27. The device according to claim 16, wherein the particle analyzer is an optical system in a epillumination mode and having an object of very short focal length, a transporting duct having a channel form being carved into the top surface of the device and covered by a very thin glass in an airtight manner.

28. The device according to claim 27, wherein the induct branching volume is delimited by the downstream ends of the transporting channels, by the entrance of the dispensing channels, by the bottom surface of this part of the flow system, and by the lower surface of the covering glass, which covers this part of the flow system.

29. The device according to claim 16, wherein some of the ducts are used purely for dispensing purposes.

30. The device according to claim 16, wherein some of the ducts of the system are used only as control ducts, carrying no particles.

31. The device according to claim 16, wherein the control medium is injected into the dispenser duct in such a manner that the amount of the fluid substance to be processed is of a minimum value, that is, the control medium is injected partly into the duct branching volume, which is located immediately in front of the entrance of the duct, and partly into the duct itself.

32. The device according to claim 31, wherein the control medium is injected to an optimum part through an injection duct, having its entrance outside of the device where the injection is carried out by an electromechanical valve.

33. The device according to claim 32, wherein the control medium is a suitable gas whereby the speed of operation of the device is higher relative to a fluidous control medium.

34. The device according to claim 32, wherein the control medium is chosen so that a prescribed mixing occurs between the control medium and the fluid substance to be dispensed and mixed.

35. The device according to claim 32, wherein the fluid substance to be dispensed is a fluid which is not to be diluted during the dispensing process, an inert gas being used as the control medium.

36. The device according to claim 16, and further comprising means for producing a vacuum in front of the entrance of one of the dispenser duct and control duct, the control medium being a gas generated by a suitable physical process.

37. The device according to claim 36, wherein the gas is generated at said optimal place between platinum electrodes through electrolysis.

38. The device according to claim 36, wherein a vapor for the control medium is generated at said optimal place between at least two noncorrosive metals, through electrical arcs or sparks between said metals, by heating up a small volume of the fluid in front of the entrance of the dispenser duct to the boiling temperature.

39. The device according to claim 36, wherein a vapor for the control medium is generated at said optimal place by illuminating the fluid at said place by a sufficiently intense light beam so as to heat said fluid to evaporation.

40. The device according to claim 16, 29 or 30, wherein one of the dispensing and control duct has a minimum length so that the downstream end of the control medium does not reach the downstream end of the duct during the process of injection of the control medium.

41. The device according to claim 16, wherein the buffer cavity is constructed into the body of the device at the downstream end of the corresponding control/dispenser duct, and has a fluid-free volume substantially larger than the whole dispensing flow system, said buffer cavity having an outlet at its bottom of such a size that both the processed fluid and the gaseous control medium flow out of it without disturbing the flow of each other, whereby both the pressure difference and the fluid flucutations are compensated to a very high degree.

42. The device according to claim 16, wherein the buffer cavity is manufactured into the body of the device at the downstream end of the control/dispensing duct carrying the processed particles, said cavity having a fluid-free volume many times larger than that of the whole dispensing flow system, and having an outlet at its bottom of such a size that said outlet does not let the gaseous control medium flow through it where the processed particles leave said cavity but through the effect of buoyancy, said control gas is forced to leave the cavity through a gas outlet hole, situated at the upper part of the cavity, which, being at the same system pressure, compensates the pressure fluctation in this cavity through its large fluid-free volume.

43. The device according to claim 16, and further comprising a body, the filtering/collector cavity being provided in the device body and comprising a cartridge equipped with a bayonet holder; an inlet tube for the substance entering into this cavity; a fine membrane filter having openings smaller than the size of the smallest particle to be filtred out of the processed substance; a rough membrane filter situated under the fine filter; a rough membrane filter situated under the fine filter; a vertical capillary system; and an outlet hole, situated at the upper part of said cylinder, for the stabilization of the pressure difference in the cavity.

44. The device according to claim 16, and further comprising a body, the filtering/collector cavity being provided in the device body and comprising a cartridge containing a bayonet system so that said cartridge is attached, airtight, into said cavity; an inlet tube provided so as to allow entry of the processed substance into the cavity; a very fine membrane with openings about no more than 1.0 micron; a rough membrane filter situated under the very fine membrane filter; a vertical cylinder having an upper end covered by a metal grid so as to support said other two filters; an opening at the upper part of said cylinder for the stabilization of the pressure in the cavity; and a second opening situated at the bottom of the vertical cylinder so as to create a sufficiently large vacuum to suck the suspending fluid and filter out the processed particles.

45. The device according to claim 16, and further comprising a main body, the filtering/collector cavity means being attached to the main device body by flexible tubes and including a bottle having a container part; an inlet tube situated at the top of the container for the entrance of the suspension into this bottle; a fine membrane filter having openings not smaller than the size of the smallest particle to be filtered out of the processed suspension; a rough membrane filter situated under the fine membrane filter; a vertical capillary sytem; and an outlet hole situated at the upper part of the bottle, for the stabilization of the pressure difference in the bottle.

46. The device according to claim 16, and further comprising a main body, the filtering/collector cavity means being attached to each particle-carrying suspension outlet of the main device body by flexible tubes and including a bottle having a container part; an inlet tube situated at the top of said bottle and oriented approximately vertically for the entrance of the processed suspension into said bottle; a very fine membrane filter having openings of no more than about 1.0 microns in diameter; a rough membrane filter situated under said very fine filter; a vertical cylinder having an upper end covered by a metal grid so as to support said two filters at the top of said cylinder; an opening at the upper part of said bottle for the stabilization of the pressure in the whole flow system; and a second opening situated at the bottom of said vertical cylinder so as to create a sufficiently large vacuum in the cylinder to suck under the suspension, fil 47. The device according to any one of claims 43–46, wherein a ring is placed at the time membrane filter so as to delimit the spreading of the filtered particles on said filter.

48. The device according to any one of claims 43–46, wherein a microscope objective holder glass is placed under said inlet tube, said glass being covered by a fine screen so that while the processed particles remain between the openings of said screen, the processed suspension itself flows under to the bottom of the bottle.

49. The device according to claim 16, wherein the vacuum, applied at its outlets, is as high as is permitted by overall construction device.

50. The device according to claim 16, wherein the dispensing ducts branch from the duct branching zone with the smallest possible angle relative to each other, while the control ducts surround these ducts, thereby obtaining an optimum duct branching geometry for the device.

51. The device according to claim 16, wherein the analyzers are of an optical type, the material of the device being a nonfluorescing, black material.

52. The device according to claim 16, wherein the whole device is made of an electrically nonconductive material.

53. The device according to claim 16, wherein several cleaning ducts are formed in the device body, through which the duct branching zone is accessible by one of a jet of cleaning fluid so that extraneous materials are removable from the zone, the cleaning ducts being sealed airtight during operation of the device.

54. The device according to claim 16, wherein the channels, formed in the open surface of the device, are sealed by a very thin, microscope cover glass, using a nonfluorescing and nonreflecting black glue so that undesirable background illumination is substantially reduced.

55. The device according to claim 16, and further comprising a body, all the channels, cavities and ducts being formed in the body of the device in such a manner that any part of the flow system is clearly observable through a stereo microscope so that any extraneous piece therein is easily observable facilitating removal of such pieces form the flow system.

56. A method according to claim 1, wherein the flow of fluid substances includes one of the fluids, gases, and aerosols.

57. A method according to claim 1, wherein the fluid control medium is one of a fluid and a gas.

58. A method according to claim 4, wherein the remaining outlets are left at atmospheric pressure.

59. A method according to claim 7, wherein said thin streams, in a steady flow state, flow into different dispenser ducts, while in the dispensing phase, they flow into the preselected dispenser ducts.

60. A device according to claim 16, wherein the flow of fluid substances includes one of fluids, gases, and aerosols.

61. A device according to claim 16, wherein the fluid control medium is one of a fluid, a gas, and a vapor.

62. A device according to claim 38, wherein the noncorrosive metals are from a group including wolfram, molybdenum and platinum.

63. A device according to claim 39, wherein the light beam is a laser beam.

64. A device according to claim 43, wherein the vertical capillary system is a bundle of glass tubes each having a diameter of approximately 1.0 mm.

65. A device according to claim 45, wherein the vertical capillary system is a bundle of glass tubes, each having a diameter of approximately 1.0 mm, held together by elastic bands.

66. A device according to claim 16, wherein the analyzers are of an optical type, the walls of the ducts and channels being covered by a very thin sheet of a nonfluorescing, black material.

67. A device according to claim 16, wherein various electrical wires incorporated into the device are well insulated from a conductive body of the device.

68. A device according to claim 54, wherein the black glue is an epoxy.

69. A device according to claim 16, wherein the analyzing apparatus is an electronic system which in the dispensing mode of continuous substances has a predetermined format for determining the distribution of the substances.

70. A method according to claim 1, wherein a first electronic system determines the proper dispensing flow configuration, and a second electronic system determines the proper flow configuration.

71. The device according to claim 16, wherein several cleaning ducts are formed in the device body so that the duct branching zone is accessible by a cleaning thread so that extraneous materials are removable from the zone, the cleaning ducts being sealed air-tight during operation of the device.

* * * * *